United States Patent
Bergamasco et al.

(10) Patent No.: US 7,249,422 B2
(45) Date of Patent: Jul. 31, 2007

(54) DEVICE BY GIONIOMETRIC MEASUREMENTS

(76) Inventors: Massimo Bergamasco, V. Don Minzoni, 144 56011 Castelmaggiore-Calci (IT); Fabio Salsedo, Viale Umberto Primo, 10004100 Latina (IT); Guenther Nino Ullrich, Viale Triesre, 354100 Massa (IT); Paolo Villella, Via Gentileschi, 856123 Pisa (IT)

( * ) Notice: Subject to any disclaimer, the term of this patent is extended or adjusted under 35 U.S.C. 154(b) by 0 days.

(21) Appl. No.: 10/540,917

(22) PCT Filed: Dec. 30, 2002

(86) PCT No.: PCT/IB02/05666

§ 371 (c)(1),
(2), (4) Date: Jul. 21, 2005

(87) PCT Pub. No.: WO2004/058065

PCT Pub. Date: Jul. 15, 2004

(65) Prior Publication Data

US 2006/0130347 A1 Jun. 22, 2006

(51) Int. Cl.
*A61B 5/103* (2006.01)
(52) U.S. Cl. .......................... 33/512; 33/1 N
(58) Field of Classification Search ............. 33/512
See application file for complete search history.

(56) References Cited

U.S. PATENT DOCUMENTS 3,991,745 A * 11/1976 Yoslow et al. ............ 33/512
4,897,927 A * 2/1990 Nicol ....................... 33/512
4,940,063 A * 7/1990 Challis ..................... 33/512
4,993,164 A * 2/1991 Jacobsen ................... 33/512
5,610,528 A * 3/1997 Neely et al. ............... 33/1 N
6,050,962 A    4/2000 Kramer et al.
6,519,862 B1 * 2/2003 Owsley et al. ............ 33/512
6,523,268 B1 * 2/2003 Boge ........................ 33/1 N
2005/0148898 A1* 7/2005 Odderson ................... 33/512

FOREIGN PATENT DOCUMENTS

WO    89/11247    11/1989

* cited by examiner

*Primary Examiner*—Christopher W. Fulton
(74) *Attorney, Agent, or Firm*—Dennison, Schultz & MacDonald

(57) ABSTRACT

A device (1) for measuring the relative orientation according to at least one degree of freedom for two objects, including a constraint generator (10) suitable for causing a goniometric sensor (40) to move in a plane, having the function of measuring the variation of relative orientation of the two objects in this plane. The goniometric sensor (40) is arranged in a housing (41) that crosses longitudinally the constraint generator (10), which has high flexional stiffness in a first longitudinal plane ($\beta$) and a low flexional stiffness in a second longitudinal plane ($\varphi$) orthogonal to the first ($\beta$). The sensor measures rotations in a plane and the constraint generator induces a rotation in that plane. With the device (1) a data suit (50) can be made for measuring the movement of limbs of an individual. For example, arranging three devices (10a, 10b, 10c) in series, but capable of measuring angles in orthogonal planes, the rotation can be measured of the arm (76) with respect to a shoulder (75) of an individual.

13 Claims, 6 Drawing Sheets

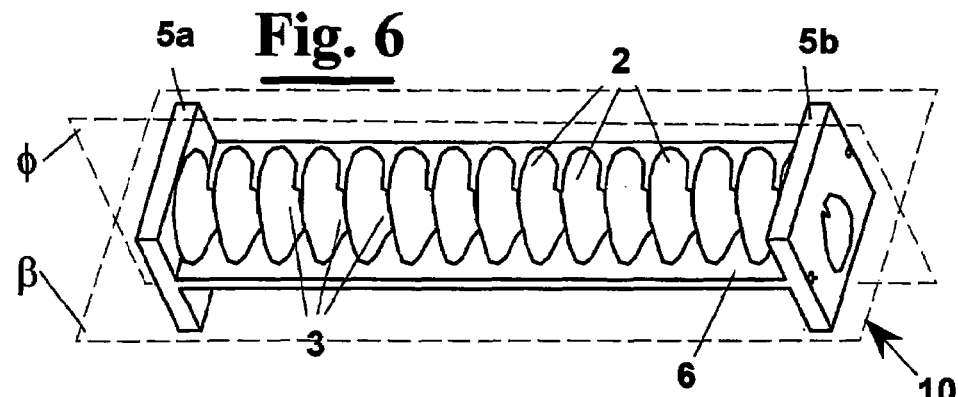
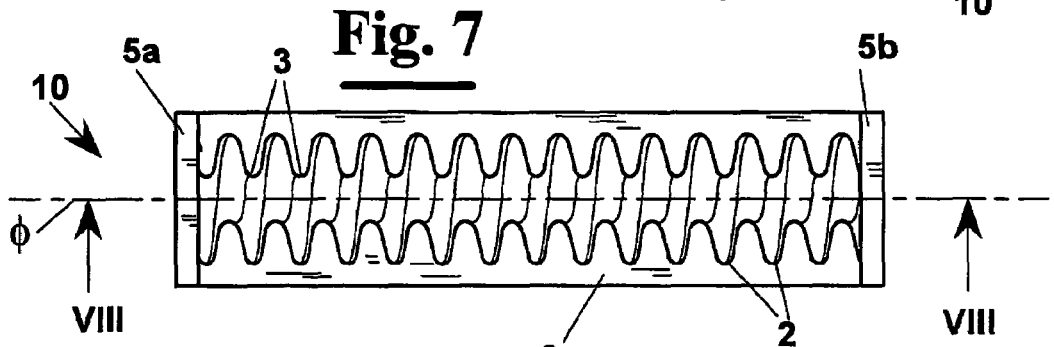
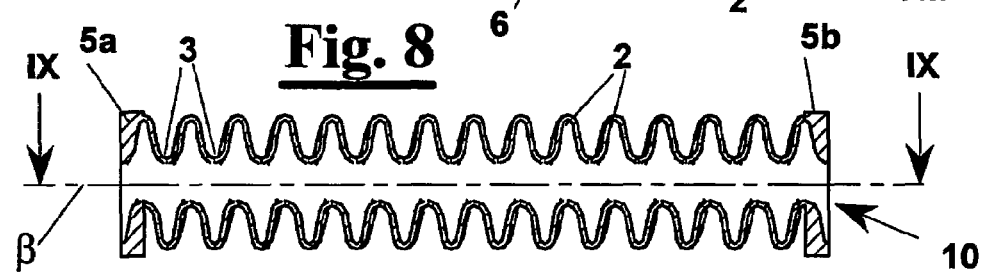
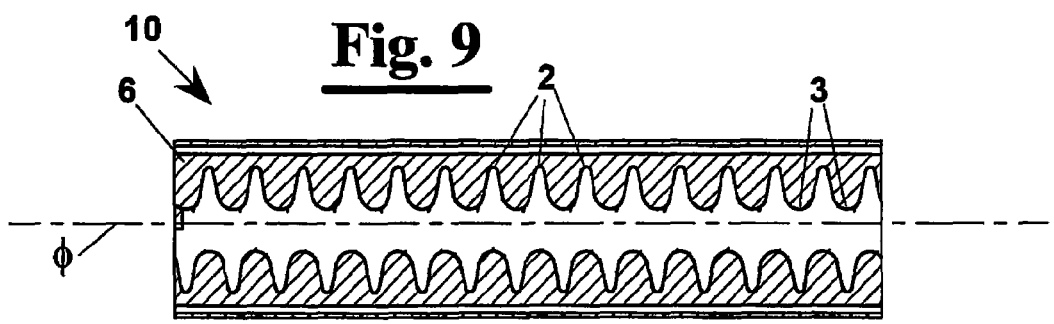
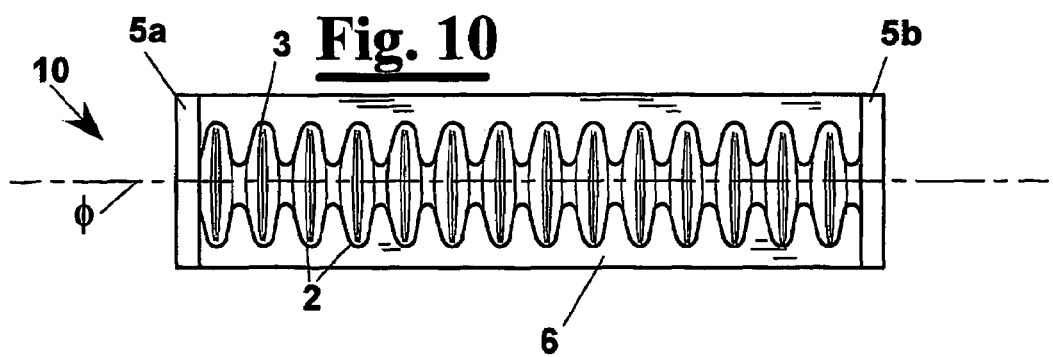

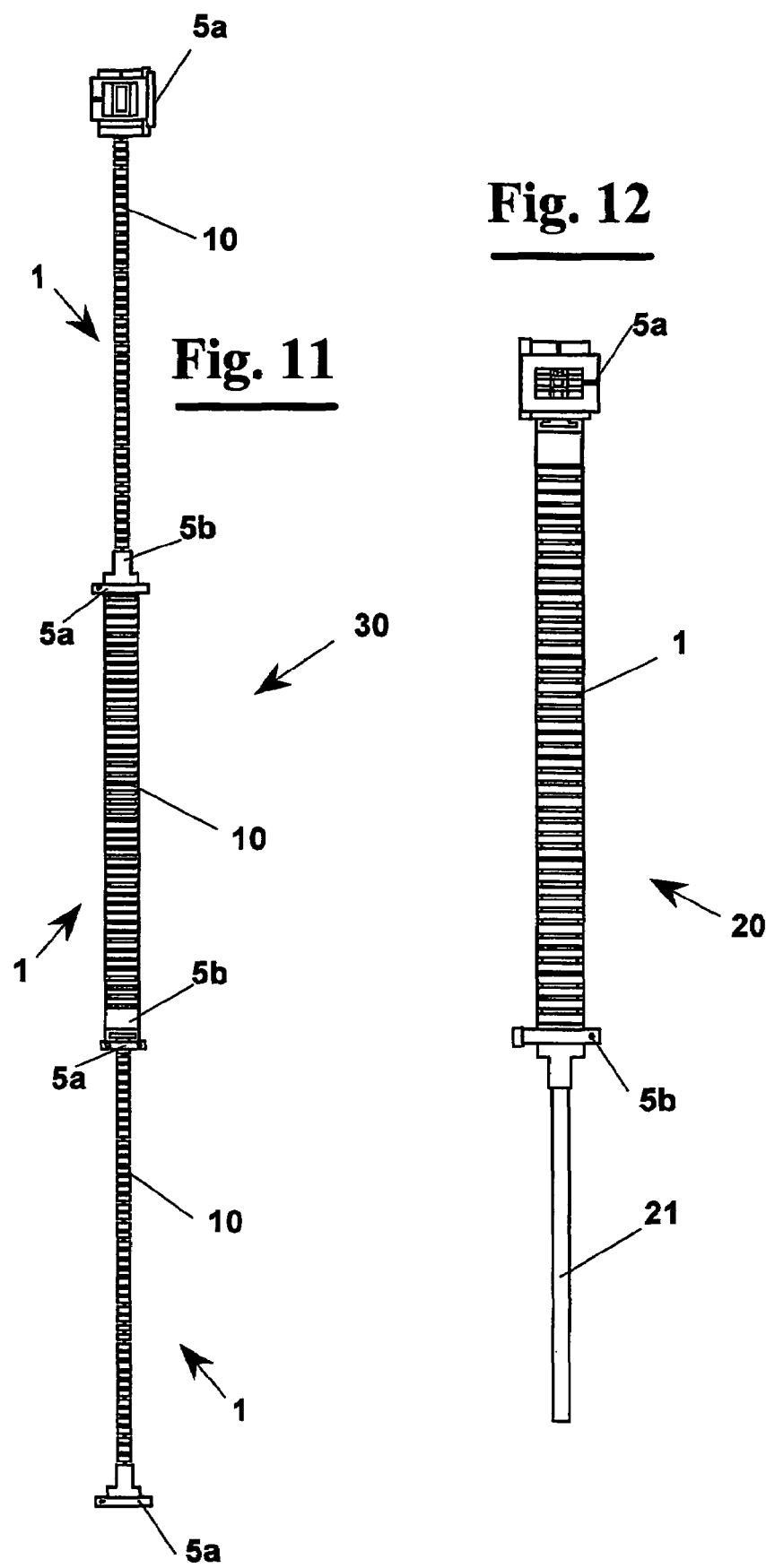

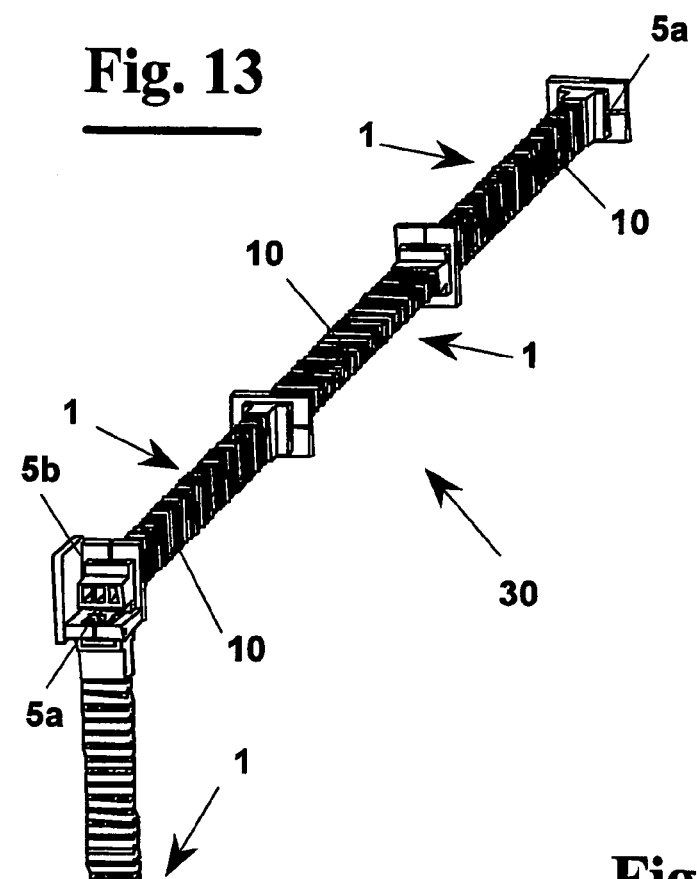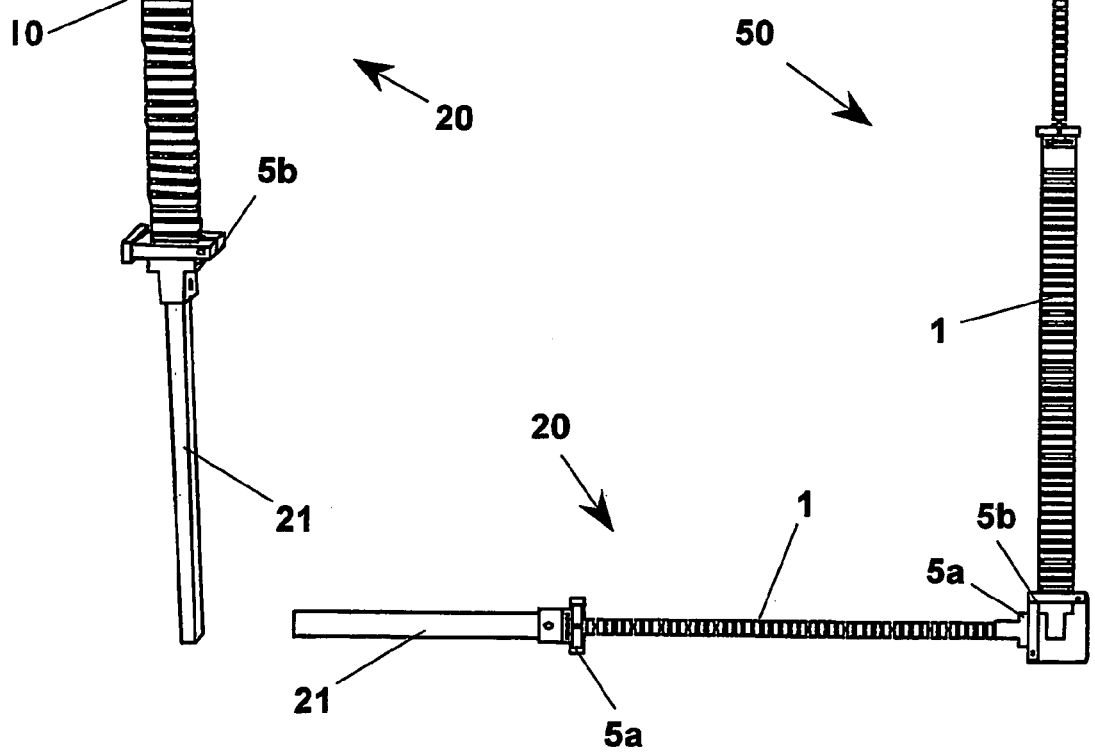

DEVICE BY GIONIOMETRIC MEASUREMENTS

FIELD OF THE INVENTION

The present invention generally relates to a device for determining the angular position of an object.

In particular, the invention relates to a device for determining the relative angular position between two objects articulated to each other with at least one degree of freedom.

Furthermore, the invention relates in particular, but not exclusively, to a device for determining the relative angular position of two limbs of the human body, for example the arm and the shoulder, the forearm and the arm, the wrist and the elbow, etc.

BACKGROUND OF THE INVENTION

The angular movements between objects that have one or more degrees of freedom are measurable with complex devices of various structure of mechanical, optical, electromagnetic nature, etc.

One of the fields in which the angular measures are very important is that of the study of the posture of the human body by measure and control of absolute position data of single points of the body or of angular relative position of two adjacent limbs. On the basis of the data recorded a digital model of the human body is then created.

Many are the possible applications, such as the production of digital movies or virtual reality, as well as applications in the medical field, and deserve a space of primary importance in scientific research.

However some limits exist that define substantially the fields of applicability for each type of device. Such limits are given mainly to the size of the limb that has to be monitored and to the number of degrees of freedom of the limb same.

In particular, the limbs with greater volume, such as arms and legs, have less degrees of freedom and the devices used for detecting their motion have larger weight and encumbrance and require a higher rate of precision. The limbs with smaller volume, such as the fingers of the hands, have a higher number of degrees of freedom and the devices used for detecting their motion must have lower weight and encumbrance and require a lower rate of precision.

The least expensive devices for detecting the movement of the limbs with greater volume are of mechanical type. They provide the use of rigid parts connected with rotational and prismatic joints, measuring angular movements with potentiometers. Even if the costs of this technology are low, however the rigid structure has high encumbrance, it is heavy and the measures obtained are usually not so precise.

Also magnetic sensors exist, which-require one or more transmitters for creating a magnetic field in a determined workspace. However, they have high costs and have the further drawback of being particularly affected by the presence of metal that can distort the magnetic field.

The optical sensors, finally, require optical tracers, active or reflective, whose light is captured by cameras for then analysing the position data by means of a computer. Usually, the optical devices are less bulky of the magnetic, but their correct operation can be affected by parts of the body that cross accidentally the light path. Other drawbacks of the optical devices are high costs and the need for post-processing the measured data as well as the long set-up time for the measuring equipment.

Another system of "motion capture" for the human body is described in U.S. Pat. No. 6,050,962. It provides angular sensors of resistive type or "resistive bend sensors" arranged at the joints, associated to auxiliary articulated connections formed by a plurality of links hinged in turn. The links form a chain that can rotate in a single plane. Consecutive portions of chain can rotate in different planes connected to each other by stiff or articulated junction elements. The angular sensors are in particular resistive segments that measure the rotations of the limbs to which they are applied, or of portions of them. The resulting device is structurally complex and expensive.

SUMMARY OF THE INVENTION

It is therefore an object of the present invention to provide a device for measuring the relative orientation of at least a first object with respect to a second object, in particular but not exclusively limbs of the human body, which is structurally easy and inexpensive to manufacture, and that does not present the drawbacks of the prior art.

It is another object of the present invention to provide such a device that is light and has low encumbrance.

It is a further object of the present invention to provide such a device that is capable of measuring the angular rotation with sufficient precision.

These and other objectives are accomplished by the device for measuring the relative orientation of at least a first object with respect to a second object free from said first object, or connected to it but with independent movement, wherein said orientation is carried out according to at least one degree of freedom comprising:
  at least one goniometric sensor for said or each degree of freedom suitable for measuring the variation of orientation in a plane;
  at least one constraint generator for said or each goniometric sensor for causing the latter to move in said plane;
  whose characteristic is that said or each constraint generator is an elongated flexible element, having a longitudinal axis, with a flexional stiffness remarkably lower in a first plane passing through the said axis and a flexional stiffness remarkably higher in a second plane orthogonal to said first plane and passing through the said axis, whereby said element is substantially flexible only in said first plane. Furthermore, said flexible element has also high stiffness to torsion and to elongation.

In particular, the goniometric sensor measures the relative angular movement of the two objects in the bending plane of the constraint generator.

Advantageously, said or each goniometric sensor is located in a housing that crosses longitudinally said constraint generator.

Alternatively, the sensor is made in the flexible element same.

Advantageously, said or each constraint generator has a plurality of substantially parallel portions having larger cross section alternated to portions coaxial to the previous but with smaller cross section.

In a first embodiment, at the portions having smaller cross section flexible elements are arranged, or lamellar hinges, suitable for allowing the mutual rotation of said portions having larger cross section only in the bending plane of the constraint generator.

Alternatively, said or each constraint generator is a plate shaped element from which projections extend substantially bellow-like. In particular, said bellow-like projections have structure chosen among: helical; alternated annular portions having larger and smaller cross section.

Preferably, the constraint generator has flanges at its ends orthogonal to said axis for connecting more constraint generators 1 in series or for connecting to the objects whose rotation must be detected.

Preferably, the goniometric sensor for measuring the relative rotation of the ends of said constraint generator comprises:

a flexible elongated element that extends between said ends, said element having a neutral axis which does not change its own length when bending, and at least one fibre spaced apart from said neutral axis and that extends from said first to said second object;

means for measuring the length variation of said fibre as the relative rotation varies between said first and said second object, said relative rotation being proportional to said length variation.

According to a particular aspect of the invention, when said first object can rotate about more axes with respect to said second object, the use is provided of a plurality of constraint generators connected rigidly in series at the respective ends and in particular a constraint generator for each axis of rotation, or rotational degree of freedom, and oriented according to different planes of flexion, so that each sensor present in the corresponding constraint generator measures the bending in a different plane. In this case the relative rotational movement of the first object with respect to the second object is computed combining the measures of angular movements in each flexion plane.

This solution can be used, for example, if the movement has to be measured of the shoulder of an individual with respect to another point of the body. In this case, considering the rotational constraint of the arm with respect to the shoulder as a ball joint, a device can be used for measuring the rotation of the arm with respect to the shoulder comprising in series three constraint generators integrated to three goniometric sensors according to the invention. The first has a free end integral to the shoulder and is oriented for bending in a first plane, the second in a second plane orthogonal to the first and the third in a third plane orthogonal to the second with its free end integral to the arm.

Moreover, a device for measuring the rotation of the forearm with respect to the arm comprises a constraint generator and a relative goniometric sensor, with an end integral to the arm and the other end integral to the forearm.

A particular aspect of the invention relates to a device for measuring the rotation of the wrist of an arm comprising at least one goniometric sensor as above described. In particular, said or each goniometric sensor is arranged with an end integral to the wrist and with the other end constrained to a second point of the arm that during the rotation of the wrist remains substantially fixed, for example to the elbow. Therefore, the goniometric sensor measures the rotation of the wrist with respect to the second point of the arm.

According to another particular aspect of the invention, a data suit for measuring the angular rotation of the arm with respect to the shoulder, of the forearm and of the wrist with respect to the arm of an individual comprises:

a device for measuring the rotation of the arm with respect to the shoulder as above described;

a device for measuring the rotation of the forearm with respect to the arm, as above described, arranged orthogonally to said device for measuring the rotation of the arm with respect to the shoulder;

a device for measuring the rotation of the wrist, as above described, having an end rigidly connected to said device for measuring the rotation of the forearm with respect to the arm.

BRIEF DESCRIPTION OF THE DRAWINGS

Further characteristics and the advantages of the device according to the present invention will be made clearer with the following description of an embodiment, exemplifying but not limitative, with reference to the attached drawings, wherein:

FIG. 6 shows a perspective view of a different embodiment of the constraint generator of FIG. 1;

FIG. 7 shows a top plan view of the constraint generator of FIG. 6;

FIG. 8 shows a longitudinal sectional view according to arrows VIII-VIII of FIG. 7 of the constraint generator of FIG. 6;

FIG. 9 shows a longitudinal sectional view according to arrows IX-IX of FIG. 8 of the constraint generator of FIG. 6;

FIG. 10 shows a top plan view of a not helical embodiment of the constraint generator of FIG. 6;

FIG. 11 shows a top plan view of three constraint generators rigidly connected and oriented on orthogonal bending planes, so that each sensor present in the relative constraint generator measures the bending occurring in the corresponding plane;

FIG. 12 shows a top plan view of a device for measuring the angular rotation of the wrist and of the forearm with respect to the arm, according to the invention;

FIGS. 13 and 14 show respectively in a perspective view and a top plan view a data suit for measuring the angular rotation of the arm with respect to the shoulder, of the forearm and of the wrist with respect to the arm of an individual, according to the invention;

FIG. 16 shows diagrammatically in a perspective elevational side view the data suit of FIG. 12 that an individual has put on;

DESCRIPTION OF A PREFERRED EMBODIMENT

In FIGS. 1 to 5 a device 1 is shown, according to the invention, for measuring the relative orientation according to at least one degree of freedom of two separated objects, or connected objects but having independent movement. It comprises a constraint generator 10 suitable for causing a goniometric sensor 40 to move in a plane for measuring the variation of relative orientation of the two objects in that plane.

Figure 2:
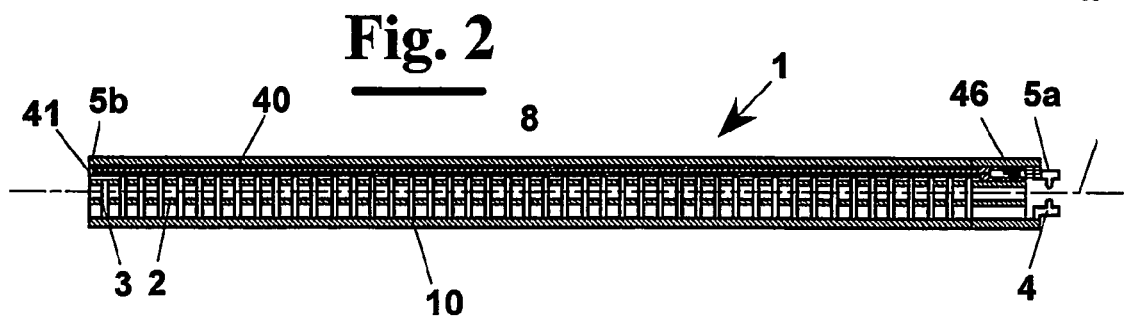
FIG. 2 shows a longitudinal sectional view according to arrows II-II of the constraint generator of FIG. 1.
Figure 3:
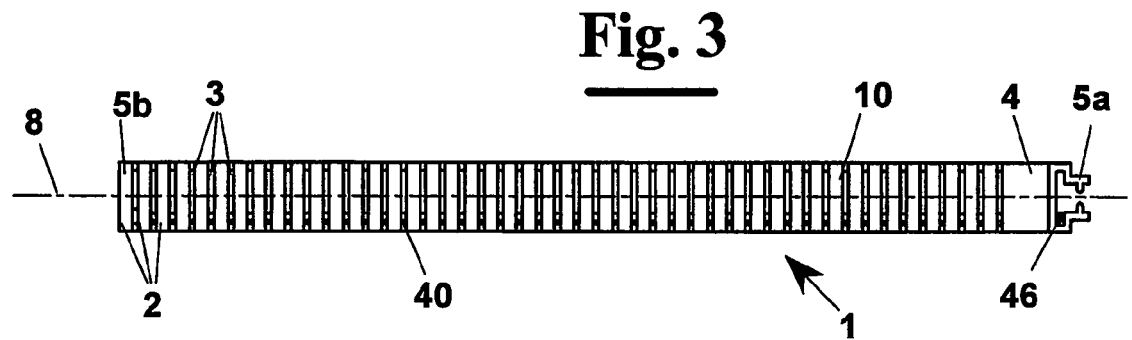
FIG. 3 shows an elevational side view of the constraint generator of FIG. 1.
Figure 4:
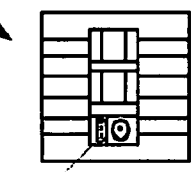
FIG. 4 shows an elevational front view of the constraint generator of FIG. 1.
Figure 15:
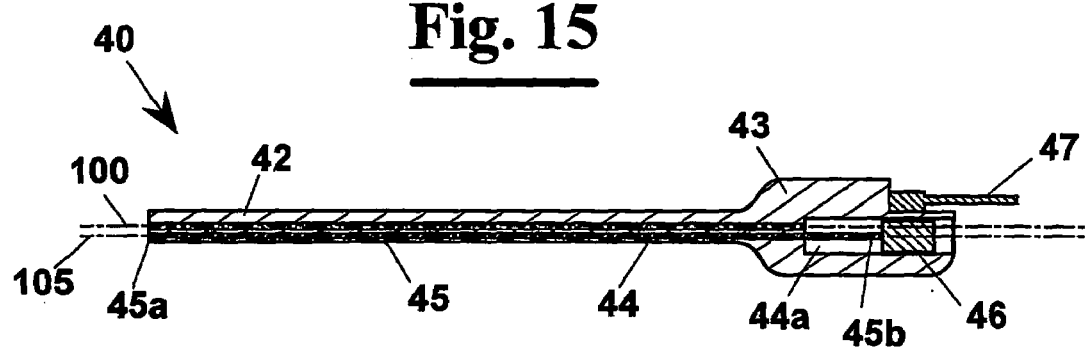
FIG. 15 shows a longitudinal sectional view of a possible embodiment of a goniometric sensor suitable for being arranged in the constraint generator of FIG. 1 or of FIG. 6.

As shown in the cross sectional view of FIG. 2, goniometric sensor 40 is arranged in a housing 41 that crosses longitudinally constraint generator 10. A type of goniometric sensor is shown in FIG. 15, and described hereinafter.

Figure 5:
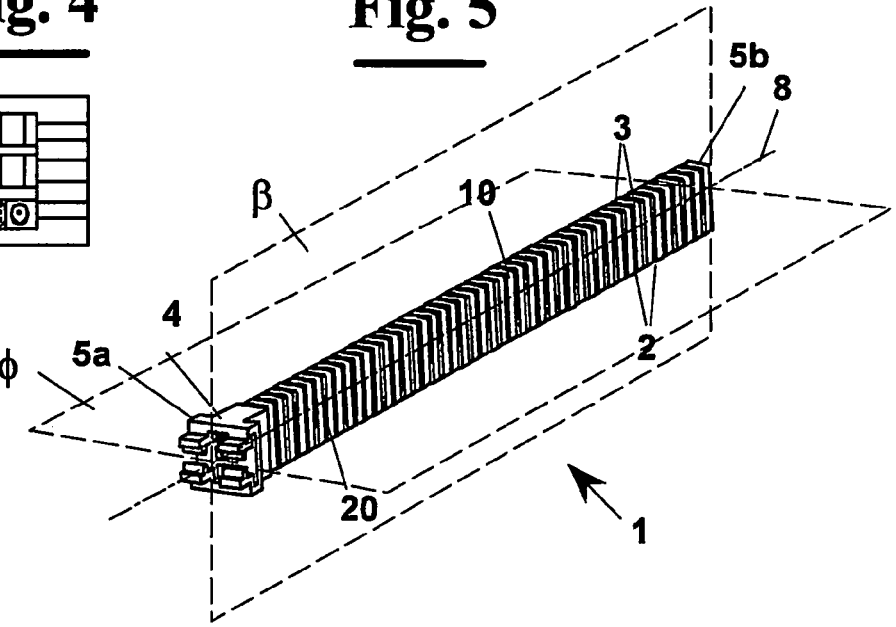
FIG. 5 shows a perspective view of the constraint generator of FIG. 1.

With reference to FIG. 5, constraint generator 10 has a longitudinal axis 8 and is equipped with a high flexional stiffness when bending in a first plane β passing through that axis 8 and a low flexional stiffness when bending in a second plane φ orthogonal to plane β and passing through axis 8 same. Therefore, constraint generator 10 is flexible only in plane φ and goniometric sensor 40 measures the relative angular movement of the two objects in this plane.

Figure 1:
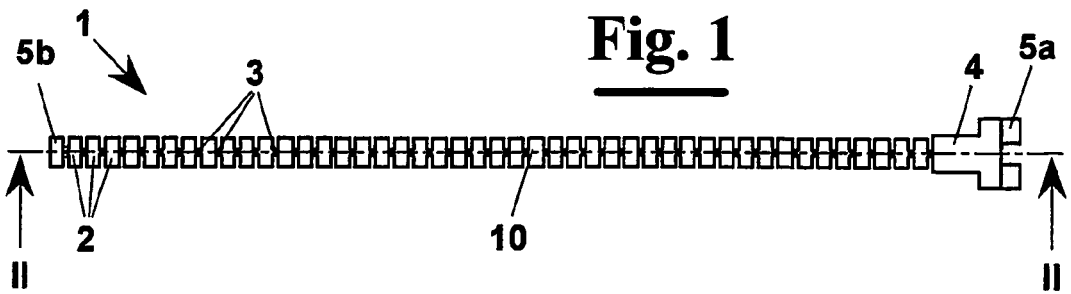
FIG. 1 shows a top plan view of a constraint generator according to the invention.

Always with reference to FIG. 1, constraint generator 10 has a plurality of substantially parallel portions having larger cross section 2 alternated to a plurality of portions coaxial to the previous having smaller cross section 3. In particular, the portions having smaller cross section 3 allow bending and cause the mutual rotation of the portions having larger cross section 2 only in bending plane φ of constraint generator 10. In particular, narrower zones 3 are made as lamellar hinges that extend in or parallel to plane β, and then allow bending only in plane φ. At the ends fastening flanges 5a and 5b are provided, for either connecting the constraint generators 1 in series according to orthogonal planes, or connecting the constraint generators to the objects whose rotation must be detected.

In an alternative embodiment of the invention and shown in FIGS. 6 to 10, constraint generator 10 can comprise a plate-shaped portion 6, with larger dimensions parallel to plane β and lower dimension in plane φ. From plate-shaped portion 6 substantially bellow like projections 2 extend that are arranged helically in axial direction. At the end of plate 6 fastening flanges 5a and 5b orthogonal to plate 6 same can be, furthermore, provided.

Alternatively, as shown in FIG. 10, the bellow-like shape is obtained by a plurality of rings alternated of diameter higher 2 and lower 3 that project from plate 6.

In both cases, plate-shaped portion 6 has flexional stiffness remarkably higher in plane β, and can bend in plane φ to it orthogonal. Furthermore, the bellow like structure increases the torsional stiffness.

The constraint generator according to the invention in the various embodiments, and made in other equivalent ways, can be manufactured directly by moulding in a single element of plastics.

In FIG. 15 in a longitudinal sectional view a possible embodiment of goniometric sensor 40 is shown. On sensor 40 a neutral axis 100 in case of bending does not change its own length, and with numeral 105 a line is indicated eccentric to the neutral axis. When the two objects of whose relative orientation has to be determined rotate reciprocally, then flexible elongated element 42 is subject to a bending that produces a length variation of the fibres not located at neutral axis 100. In particular, the fibre located at eccentric line 105 is subject to a length variation ΔL. This length variation of fibre 105 can be determined by means of a sensor 47, for example a Hall effect sensor, which detects the movement of a cable 45 located in a channel 44 made in the element end 42. In particular, sensor 47 measures the movement of a magnet 46 connected to an end of cable 45 and sliding in an enlarged portion 44a of channel 44.

The goniometric sensor can be inserted after the moulding of the constraint generator or embedded in the plastic matrix of the constraint generator. In a further embodiment, the goniometric sensor is made directly in constraint generator 10, carrying out a measure of lengthening of a fibre different from the neutral axis of constraint generator 10 same, in a way similar to the goniometric sensor shown above.

The type of goniometric sensor used, obviously, is exemplifying and not limitative, and goniometric sensors of other type can be used capable of measuring the rotation of the two ends of constraint generator 10.

According to a particular aspect of the invention, if the orientation has to be measured of a first object capable of rotating about three axes with respect to a second object, the use is provided of three constraint generators 10 connected rigidly in series at the ends 5 (FIG. 11). In particular, the three constraint generators 10 are oriented according to the different bending planes, so that each sensor 40 present in the corresponding constraint generator 10 measures the bending in a different plane. Therefore, the relative rotational movement of the first object with respect to the second object is computed, in this case, combining the measures of angular movements in each flexion plane.

Figure 16:
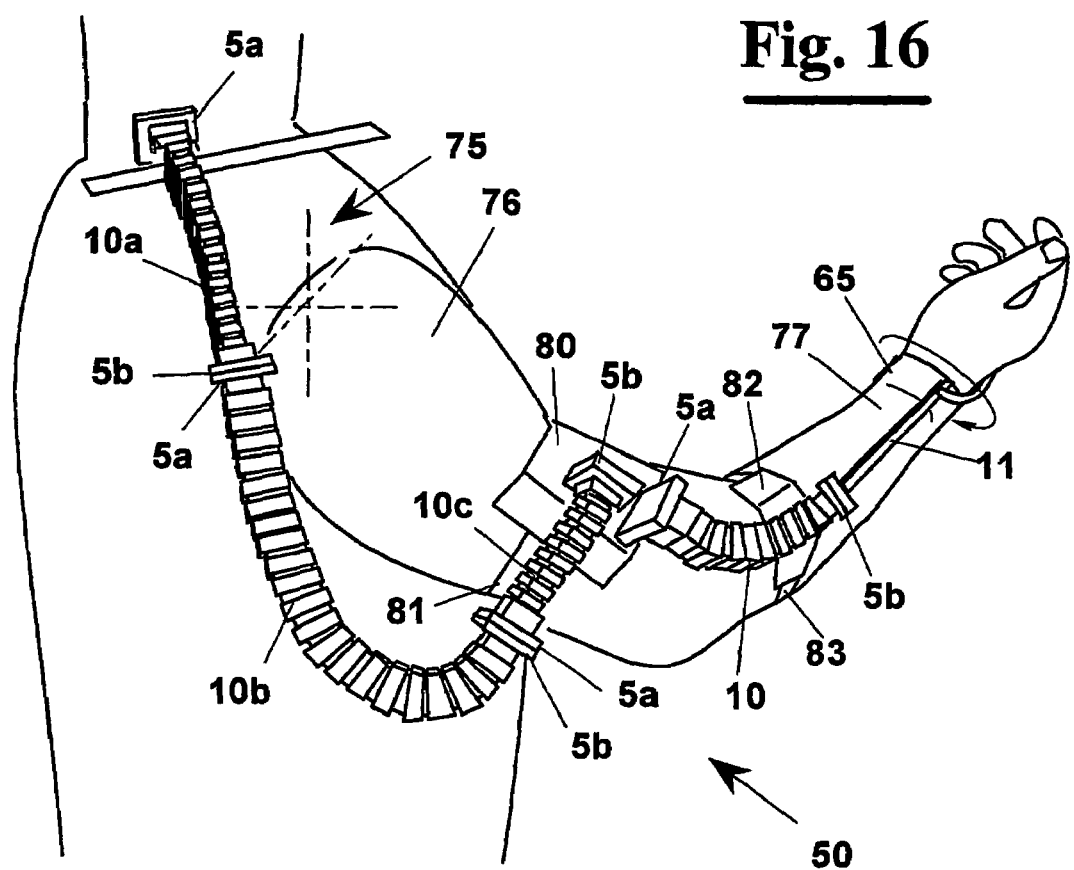

This solution can be, for example, used for measuring the movement of arm 76 of an individual with respect to the shoulder (FIG. 16). In this case, considering the movement of the arm with respect to the shoulder 75 as a spherical movement characterised by 3 independent degrees of freedom, such rotations are measurable with device 50 for measuring the rotation of arm 76 with respect to shoulder 75, comprising the three constraint generators 10 in series and the relative three goniometric sensors 40 to it associated.

Always with reference to FIG. 16, first constraint generator 10a has a free end 5a integral to shoulder 75 and is oriented for bending in a first plane. Second constraint generator 10b has end 5a rigidly connected to end 5b of first generator 10a and is oriented for bending in a second plane orthogonal to the first flexion plane. Third constraint generator 10c has in turn an end 5a rigidly connected to end 5b of second generator 10b, it is oriented for bending in a third plane orthogonal to the second bending plane and has the free end 5b connected to a support 80 integral to arm 76 by means of a belt 81.

Figure 17:
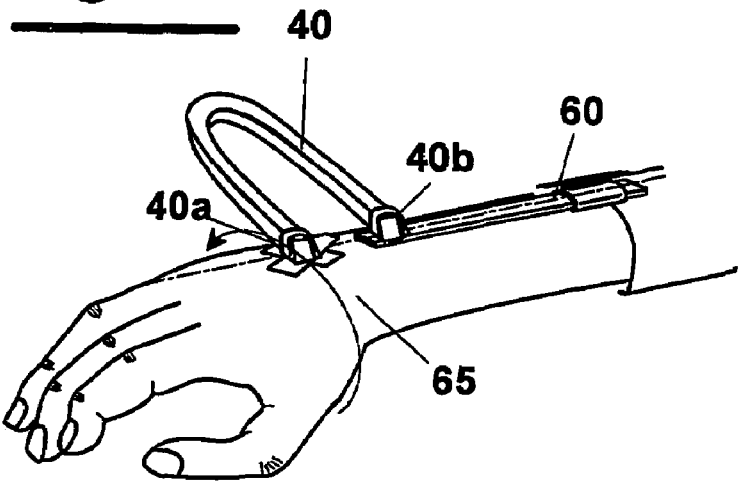
FIGS. 17 to 19 show a perspective view of a possible embodiment of a device for measuring the rotation of the wrist, according to the invention.
Figure 18:
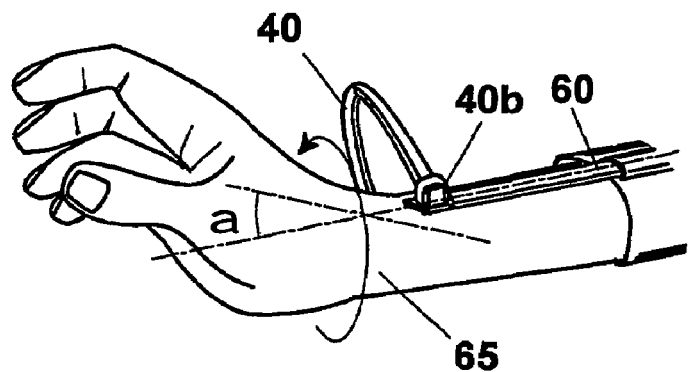
Figure 19:
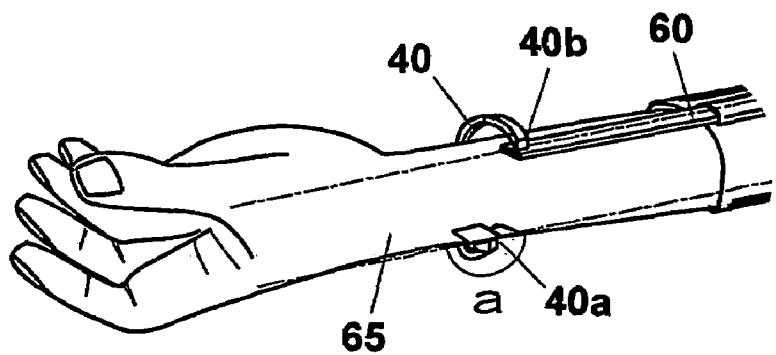

Similarly, a device 20 for measuring the rotation of forearm 77 with respect to arm 76 comprises a constraint generator 10 and a relative goniometric sensor 40. In this case, a first end 5a of constraint generator 10 is mounted on a support 80 integral to arm 76 by means of a belt 81 and the other end 5b is fixed to a support 82 integral to forearm 77 by means of a belt 83 (FIG. 16). Finally, if at end 5b of device 20 a rod 31 is connected, as detailed in FIGS. 17 to 19, having a free end at the wrist 65 and provided with a goniometric sensor 40 (with or without constraint generator), it is possible to measure also the rotation of the wrist 65 with respect to arm 76.

Notwithstanding reference has been made mainly to the movement of an arm with respect to a shoulder, a forearm and a wrist, the above mentioned device can be easily implemented by a skilled person for measuring the motion of other parts of the body such as legs, head, trunk, etc.

The foregoing description of a specific embodiment will so fully reveal the invention according to the conceptual point of view, so that others, by applying current knowledge, will be able to modify and/or adapt for various applications such an embodiment without further research and without departing from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. Device for measuring relative orientation of at least a first object with respect to a second object free from said first object, or connected to the first object but with independent movement, wherein said orientation is carried out according to at least one degree of freedom, comprising:
   at least one goniometric sensor for each said degree of freedom, constructed and arranged for measuring variation of orientation in a plane;
   at least one constraint generator for each said goniometric sensor, constructed and arranged to cause the sensor to move in said plane;
   wherein each said constraint generator comprises a flexible elongated element having a longitudinal axis with a low flexional stiffness in a first plane passing through said axis, and a high flexional stiffness in a second plane orthogonal to said first plane and passing through the axis, said element being flexible only in said first plane.

2. Device according to claim 1, wherein said constraint generator has high stiffness to torsion and to tensile stress.

3. Device according to claim 1, wherein each said goniometric sensor is disposed in a housing that crosses longitudinally said constraint generator, said goniometric sensor measuring the relative angular movement of said objects in a bending plane of said constraint generator.

4. Device according to claim 1, wherein each said constraint generator comprises a plurality of substantially parallel portions of larger cross section alternating with a plurality of portions of smaller cross section, said portions of smaller cross sections conferring to the structure a larger flexional capacity in a first plane and larger flexional stiffness in a plane orthogonal to the first plane, and a high stiffness to torsion and to tensile stress.

5. Device according to claim 1, wherein each said constraint generator comprises an plate shaped element having bellow-like projections extending therefrom.

6. Device according to claim 5, wherein said projections have structure selected from the group consisting of helical and alternating annular portions having larger and smaller cross sections.

7. Device according to claim 1, wherein at least one said constraint generator comprises flanges orthogonal to said axis for fastening at ends thereof further constraint generators in series or for fastening to objects whose rotation will be measured.

8. Device according to claim 1, wherein said goniometric sensor comprises:
   a flexible elongated element extending between a first and a second object, said element having a neutral axis which does not change in length when bending, and at least one fiber spaced apart from said neutral axis and extending from the first to the second object;
   means for measuring the length variation of said fiber as the relative rotation varies between the first and the second object, the relative rotation being proportional to said length variation.

9. Device for measuring rotation of a wrist of an individual with respect to a point on an arm of the individual, the point remaining substantially fixed during the rotation of the wrist, comprising at least one goniometric sensor according to claim 8, arranged with a first end integral to the wrist and an opposite end constrained to the fixed point, said goniometric sensor measuring the rotation of the wrist with respect to a second point of the arm.

10. Device for measuring relative orientation of a first object capable of rotating about more axes independent with respect to a second object, comprising a plurality of constraint generators according to claim 1, connected rigidly in series at ends thereof, and having one said constraint generator for each axis of rotation or rotational degree of freedom, said constraint generators being oriented according to flexion planes, such that each sensor present in a corresponding constraint generator measures bending in a different plane, the relative rotational movement of the first object with respect to the second object being determined by means of a combination of measurements of angular movements in each flexion plane.

11. Device for measuring the rotation of an arm with respect to a shoulder of an individual, comprising three constraint generators according to claim 1, arranged in series and associated with three goniometric sensors, wherein the first constraint generator has a free end integral to the shoulder and is oriented for bending in a first plane, the second constraint generator is in a second plane orthogonal to the first plane, and the third constraint generator is in a third plane orthogonal to the second and having a free end integral to the arm.

12. Device for measuring rotation of a forearm with respect to an arm of an individual, comprising a constraint generator and an associated goniometric sensor according to claim 1, with a first end integral to the arm an opposite end integral to the forearm.

13. Data suit for measuring angular rotation of an arm with respect to a shoulder, a forearm with respect to an arm, and a wrist with respect to a point of an arm of an individual, comprising:
   a device for measuring rotation of the arm with respect to the shoulder comprising three constraint generators, arranged in series and associated with three goniometric sensors, wherein the first constraint generator has a free end integral to the shoulder and is oriented for bending in a first plane, the second constraint generator is in a second plane orthogonal to the first plane, and the third constraint generator is in a third plane orthogonal to the second and having a free end integral to the arm;
   a device for measuring the rotation of the forearm with respect to the arm, comprising a constraint generator and an associated goniometric sensor, with a first end integral to the arm and an opposite end integral to the forearm, arranged orthogonally to said device for measuring the rotation of the arm with respect to the shoulder; and
   a device for measuring the rotation of the wrist, comprising at least one goniometric sensor, arranged with a first end integral to the wrist and an opposite end constrained to the fixed point, said goniometric sensor measuring the rotation of the wrist with respect to the second point of the arm arranged with an end integral to the wrist and with the other end constrained to said fixed point, said goniometric sensor measuring the rotation of the wrist with respect to said second point of the arm,
   wherein each said constraint generator comprises a flexible elongated element having a longitudinal axis with a low flexional stiffness in a first plane passing through said axis, and a high flexional stiffness in a second plane orthogonal to said first plane and-passing through the axis, said element being flexible only in said first plane.

* * * * *